United States Patent [19]

Banks

[11] Patent Number: 5,556,868
[45] Date of Patent: Sep. 17, 1996

[54] ANTIPARASITIC AVERMECTIN AND MILBEMYCIN DERIVATIVES

[75] Inventor: Bernard J. Banks, Sandwich, United Kingdom

[73] Assignee: Pfizer Inc, New York, N.Y.

[21] Appl. No.: 302,655

[22] PCT Filed: Feb. 23, 1993

[86] PCT No.: PCT/EP93/00423

§ 371 Date: Sep. 28, 1994

§ 102(e) Date: Sep. 28, 1994

[87] PCT Pub. No.: WO93/18041

PCT Pub. Date: Sep. 16, 1993

[30] Foreign Application Priority Data

Mar. 7, 1992 [GB] United Kingdom .................. 9205007

[51] Int. Cl.⁶ ......................... A61K 31/335; A61K 31/70
[52] U.S. Cl. ........................... 514/450; 514/30; 549/264; 536/7.1
[58] Field of Search ............... 549/264; 514/450, 514/30; 536/7.1

[56] References Cited

U.S. PATENT DOCUMENTS

| | | | |
|---|---|---|---|
| 4,423,209 | 12/1983 | Mrozik | 536/7.1 |
| 4,929,638 | 5/1990 | Dutton et al. | 514/450 |
| 4,980,370 | 12/1990 | Dutton et al. | 514/450 |
| 4,992,424 | 2/1991 | Banks et al. | 514/30 |
| 5,030,650 | 7/1991 | Buckwalter et al. | 514/450 |
| 5,108,992 | 4/1992 | Lawrence et al. | 514/30 |
| 5,229,415 | 7/1993 | Linn et al. | 514/450 |

FOREIGN PATENT DOCUMENTS

| | | |
|---|---|---|
| 0170006 | 2/1986 | European Pat. Off. . |
| 0214731 | 3/1987 | European Pat. Off. . |
| 0254583 | 1/1988 | European Pat. Off. . |
| 0259779 | 3/1988 | European Pat. Off. . |
| 0317148 | 5/1989 | European Pat. Off. . |
| 0327270 | 8/1989 | European Pat. Off. . |
| 0335541 | 10/1989 | European Pat. Off. . |
| 0340932 | 11/1989 | European Pat. Off. . |
| 0350187 | 1/1990 | European Pat. Off. . |
| 0410615 | 1/1991 | European Pat. Off. . |
| 2329486 | 12/1973 | Germany . |
| 1390336 | 4/1975 | United Kingdom . |
| 1573955 | 8/1980 | United Kingdom . |
| 2166436 | 5/1986 | United Kingdom . |

OTHER PUBLICATIONS

*Macrolide Antibiotics*, Omura, S., Ed., Academic Press, New York (1984), Chapter 14, pp. 553–606.
Davies, H. G. et al., Natural Products Reports 3:87–121 (1986).
Davies, H. G. et al., Chem. Soc. Rev. 20:211–269 (1991).
Davies, H. G. et al., Chem. Soc. Rev. 20:271–339 (1991).
Yanai, T et al CA 113: 114954 w (1990).

*Primary Examiner*—C. Warren Ivy
*Assistant Examiner*—Amelia Owens
*Attorney, Agent, or Firm*—Peter C. Richardson; Paul H. Ginsburg; Gezina Holtrust

[57] ABSTRACT

Avermectin and milbemycin derivatives of formula (I)

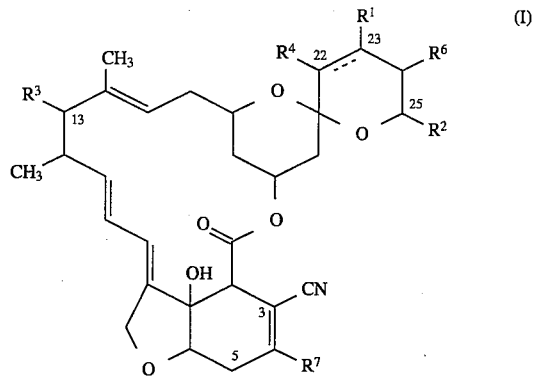

having a double bond at the 3–4 position and a cyano substituent at the 3-position have outstanding anthelmintic properties. They may be prepared by allowing an avermectin or milbemycin derivative having a leaving group at the 5-position, or having double bonds at the 2–3 and 4–5 positions and no substituent at the 5-position, to react with an ionic cyanide.

30 Claims, No Drawings

ANTIPARASITIC AVERMECTIN AND MILBEMYCIN DERIVATIVES

This application is a 371 of PCT/EP93/00423 filed Feb. 23, 1993, published as WO93/18041 Sep. 16, 1993.

This invention relates to antiparasitic agents and in particular to compounds related to the avermectins and milbemycins but having a cyano substituent at the 3-position and lacking a substituent at the 5-position.

The avermectins are a group of broad-spectrum antiparasitic agents referred to previously as the C-076 compounds. They are produced by fermenting a certain strain of micro-organism *Streptomyces avermitilis* in an aqueous nutrient medium. The preparation and structure of these compounds obtained by fermentation are described in British Patent Specification 1573955. The milbemycins are structurally related macrolide antibiotics lacking the sugar residues at the 13-position. They may be produced by fermentation, for example as described in British Patent Specification No. 1390336 and European Patent Specification No. 0170006.

In addition to these fermentation-derived products, a large number of publications describe compounds derived semisynthetically from these products, many of which possess useful antiparasitic properties. Some of this chemistry is reviewed in *Macrolide Antibiotics*, Omura S., Ed., Academic Press, New York (1984) and by Davies, H. G. and Green, R. H. in *Natural Product Reports* (1986), 3, 87–121 and in *Chem. Soc. Rev.* (1991), 20, 211–269 and 271–239.

Compounds related to the original C-076 avermectins have also been prepared by fermentation of avermectin-producing micro-organisms. For example European Patent Specifications 0214731 and 0317148 describe production of compounds related to the C-076 avermectins but having a different substituent at the 25-position by fermentation in the presence, in the fermentation medium, of certain acids.

Other publications mentioning different combinations of substituents at various positions on the avermectin or milbemycin nucleus are EP-A-317148, 340932, 335541, 350187, 410615, 259779 and 254583; DE-A-2329486 and GB-A-2166436.

The avermectins and milbemycins and their derivatives have the structure:

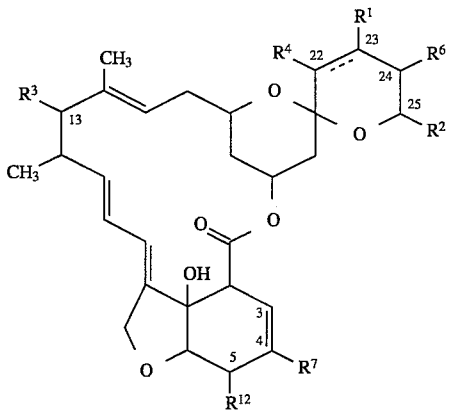

wherein the broken line represents an optional bond, $R^1$ and $R^4$ being absent when this bond is present, $R^1$, $R^3$, $R^4$ and $R^{12}$ are independently H, OH, halo, oxo, oximino or an organic radical, $R^2$ and $R^7$ are organic radicals, $R^6$ is H or an organic radical.

These compounds include the avermectins themselves and their substituted derivatives in which $R^3$ is a 4'-(α-L-oleandrosyl)-α-L-oleandrosyloxy group, optionally substituted at the 4" position; the avermectin monosaccharides and their derivatives in which $R^3$ is α-L-oleandrosyloxy, optionally substituted at the 4' position; the avermectin aglycones and their derivatives in which $R^3$ is OH or a substituent other than oleandrosyl replacing this group; and the milbemycins and their derivatives in which $R^3$ is H.

All the avermectins and structurally related milbemycins and their derivatives hitherto known have no substituent at the 3-position with a C3–C4 double bond, neither has any process capable of producing such compounds been reported.

It has now been discovered that avermectin and milbemycin derivatives having a cyano substituent at the 3-position, with no substituent at the 5-position, may be prepared and that some of these compounds have outstanding antiparasitic properties.

According to one aspect of the invention, there are provided avermectin and milbemycin derivatives having a cyano substituent at the 3-position, a double bond between the 3–4 positions and no substituent at the 5-position of the molecule.

Compounds of the invention are of formula (I):

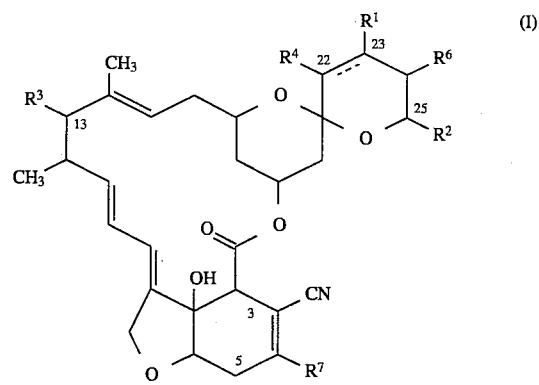

wherein the broken line represents an optional bond, $R^1$ and $R^4$ being absent when this bond is present, $R^1$, $R^3$, $R^4$ are independently H, OH, halo, oxo, oximino, or an organic radical, and $R^2$ and $R^7$ are organic radicals and $R^6$ is H or an organic radical.

Compounds according to the invention include those in which the 22–23 optional bond is present and those in which this optional bond is absent (i.e. a single bond between the 22 and 23 positions); $R^1$ is H, OH, $C_1$–$C_8$ alkoxy optionally substituted by halo or by $C_1$–$C_4$ alkoxy, $C_2$–$C_5$ alkanoyl, $C_2$–$C_5$ alkoxy carbonyl, carboxy, mercapto or by aryl, or $R^1$ is $C_3$–$C_8$ alkenyloxy, $C_2$–$C_9$ alkylcarbonyloxy or $C_3$–$C_9$ alkenylcarbonyloxy, arylcarbonyl or carbamoyl optionally substituted by a $C_1$–$C_9$ alkyl group, or $R^1$ is attached to the remainder of the molecule by a double bond and is oxo or oximino optionally O-substituted by a $C_1$–$C_8$ alkyl, alkenyl, alkynyl, trialkylsilyl or aralkyl group, or is methylene optionally substituted by a cyano or $C_1$–$C_9$ alkyl group;

$R^4$ is H, OH or $C_1$–$C_8$ alkoxy or $C_1$–$C_9$ alkanoyloxy, or is attached to the remainder of the molecule by a double bond and is =$CH_2$, oxo or oximino optionally substituted as above;

$R^2$ is (a) an alpha-branched $C_3$–$C_8$, alkyl, alkenyl (including but-2-enyl, pent-2-enyl, and 4-methylpent-2-enyl), alkoxy-alkyl, or alkylthioalkyl group; an alpha-branched $C_4$–$C_8$ alkynyl group; a ($C_4$–$C_8$)cycloalkyl-alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —$CH_2R^8$ wherein $R^8$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or partially unsaturated and which may optionally be substituted by one or more $C_1$–$C_4$ alkyl groups or halo atoms; or a group of the formula $SR^9$ wherein $R^9$ is $C_1$–$C_8$ alkyl, $C_2$–$C_8$ alkenyl, $C_3$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or a 3 to 6 membered oxygen or sulphur containing heterocylic ring which may be saturated, or fully or partially unsaturated and which may optionally be substituted by one or more $C_1$–$C_4$ alkyl groups or halo atoms; or (c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a ($C_1$–$C_6$) alkoxy-carbonyl group, said substituents on $R_2$ being attached to either or both of a terminal carbon atom and a carbon atom adjacent a terminal carbon atom of $R^2$; or (d) =$CH_2$ or a group of the formula:

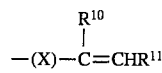

wherein $R^{10}$ and $R^{11}$ are both H; $R^{10}$ is H and $R^{11}$ is $C_1$–$C_3$ alkyl, or one of $R^{10}$ and $R^{11}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy($C_1$–$C_4$)alkyl, cyano, aminosulphonyl, $C_2$–$C_6$ alkanoyl, $C_2$–$C_6$ alkoxycarbonyl, nitro, trifluoromethyl, trifluoromethoxy, amino or mono or di($C_1$–$C_4$) alkylamino; and X is a direct bond or is an alkylene group having from 2 to 6 carbon atoms which may be straight or branched-chain; or (e) phenyl which may optionally be substituted with at least one substituent selected from $C_1$–$C_4$ alkyl, $C_1$–$C_4$ alkylthio groups, halo atoms, trifluoromethyl, and cyano;

or $R^2$ may be a group of formula (II):

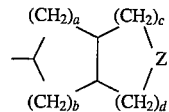

wherein Z is O, S or —$CH_2$— and a, b, c and d may each independently be 0, 1 or 2; the sum of a, b, c, and d not exceeding 5;

$R^3$ is hydrogen, hydroxy, $C_1$–$C_8$ alkoxy or alkenoxy, $C_1$–$C_9$ alkanoyloxy or alkenoyloxy, aroyloxy, oxymethyleneoxy-($C_1$–$C_5$)alkyloxy-($C_1$–$C_5$)alkyl, halogen, oxo, or optionally substituted oximino, hydrazono, carbazido or semicarbazido, N-($C_1$–$C_4$)alkyl semicarbazido, N,N-di($C_1$–$C_4$)alkylsemicarbazido, $C_1$–$C_5$ alkanoylhydrazido, benzoylhydrazido or ($C_1$–$C_4$)alkyl benzoylhydrazido; or $R_3$ is

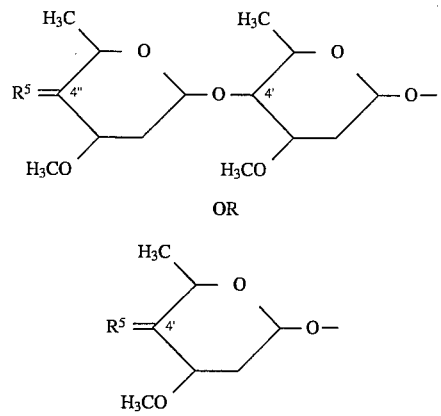

wherein $R^5$ is attached to C-4" or C-4' by a single bond and is hydrogen, halo, hydroxy, $C_1$–$C_9$ alkanoyloxy or alkenoyloxy, aroyloxy, $C_1$–$C_8$ alkoxy, amino, N-($C_1$–$C_8$) alkylamino, N,N-di($C_1$–$C_9$) alkylamino, N-($C_1$–$C_5$)alkanoylamino, or N,N-di($C_1$–$C_9$) alkanoylamino; or $R^5$ is attached to C-4" or C-4' by a double bond and is oxo, optionally substituted oximino, semicarbazido, N-($C_1$–$C_4$) alkylsemicarbazido, N,N-di($C_1$–$C_4$)alkylsemicarbazido, ($C_1$–$C_5$) alkanoylhydrazido, benzoylhydrazido, or ($C_1$–$C_4$)alkylbenzoylhydrazido; $R_6$ is H or $C_1$–$C_6$ alkyl; and $R_7$ is methyl, hydroxymethyl, ($C_1$–$C_4$ alkoxy)methyl, ($C_2$–$C_5$ alkanoyl) oxymethyl, ($C_2$–$C_5$ alkenoyl)oxymethyl, aroyloxymethyl, aralkanoyloxymethyl, oxo, optionally substituted oximino, halomethyl, azidomethyl or cyanomethyl.

Compounds of the invention include those in which $R^1$ is H, OH, O-($C_1$–$C_4$)alkyl, O-($C_1$–$C_5$)alkanoyl, oxo and oximino optionally substituted by $C_1$–$C_4$ alkyl or aryl($C_1$–$C_4$)alkyl; those in which $R^2$ is straight or branched-chain alkyl, alkenyl, cycloalkyl or cycloalkenyl (including methyl, ethyl, 2-propyl, 2-butyl, 2-buten-2-yl, 2-penten-2-yl, 4-methyl-2-penten-2-yl and cyclohexyl); those in which $R^4$ is H, OH, oxo or oximino; and those in which $R^3$ is H or is of formula:

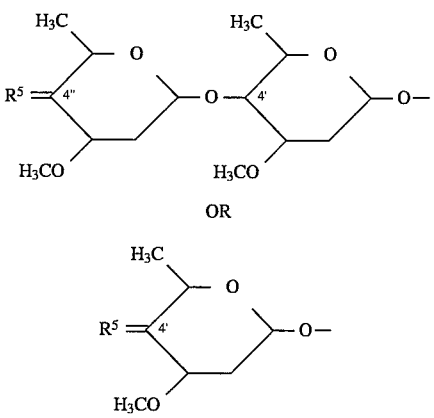

where $R^5$ is OH, ($C_1$–$C_4$) alkoxy, ($C_2$–$C_5$) alkanoyloxy, amino, N-($C_1$–$C_4$) alkylamino, N-($C_1$–$C_5$)alkanoylamino, oxo or oximino optionally substituted by a $C_1$–$C_4$ alkyl group.

In all the above definitions, unless the context requires otherwise, alkyl groups containing 3 or more carbon atoms may be straight or branched-chain; halo means fluoro, chloro, bromo or iodo; and aryl means phenyl optionally substituted by one or more $C_1$–$C_4$ alkyl or $C_1$–$C_4$ alkoxy groups or halo atoms.

Compounds within the scope of the invention include:

(i) 3-cyano-5-deoxy-25-cyclohexyl avermectin B2 or its monosaccharide, or (ii) 3-cyano-5-deoxy-23-methoxy-25-cyclohexyl-22,23-dihydroavermectin B1 or its monosaccharide, or (iii) 4''-oximino-3-cyano-5-deoxy-23-methoxy-25-cyclohexyl- 22,23-dihydroavermectin B1; or (iv) 3-cyano-5-deoxy-25-cyclohexyl-22,23-dihydroavermectin B1 or its monosaccharide, or (v) 4,-epi-hydroxy-3-cyano-5-deoxy-25-cyclohexyl-22,23-dihydroavermectin B1 monosaccharide, or (vi) 23-methoximino-3-cyano-5-deoxy-25-cyclohexyl-22,23-dihydroavermectin B1 or its monosaccharide; or (vii) 3-cyano-5-deoxy-25-cyclohexylavermectin B1 or its monosaccharide; or (viii) 3-cyano-5,13-dideoxy-23-methoxy-25-cyclohexyl-22,23-dihydroavermectin B1 aglycone; or (ix) 3-cyano-5,13-dideoxy-25-cyclohexyl-22,23-dihydro avermectin B1 aglycone; or (x) 3-cyano-5-deoxy-milbemycin D.

The avermectins and monosaccharides are generally preferred over the aglycones and milbemycins and their derivatives having no saccharide groups at the 13-position.

It will be understood that the compounds of the invention include several asymmetric centres and accordingly may exist as several pairs of stereoisomers. The invention includes all such stereoisomers, whether separated or not.

A further aspect of the invention provides a method of making such an avermectin or milbemycin derivative which comprises allowing an avermectin or milbemycin derivative substituted at the 5-position with a leaving radical, or having no substituent at the 5-position and double bonds at the 2–3 and 4–5 positions, to react with an ionic cyanide.

Derivatives having double bonds at the 2–3 and 4–5 positions are of formula (II):

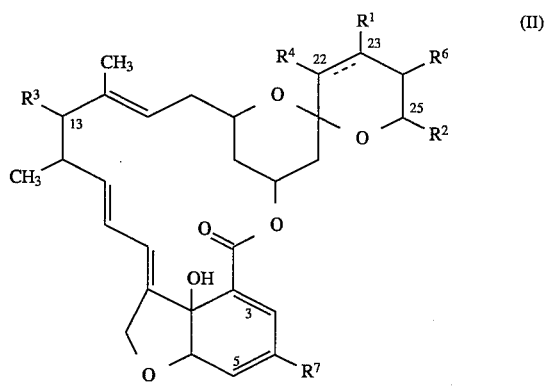

where $R^1$, $R^2$, $R^3$, $R^4$, $R^6$ and $R^7$ are as defined above. The compounds of the formula (II) are themselves novel.

The compound of formula (II) may be prepared from a compound of formula (III):

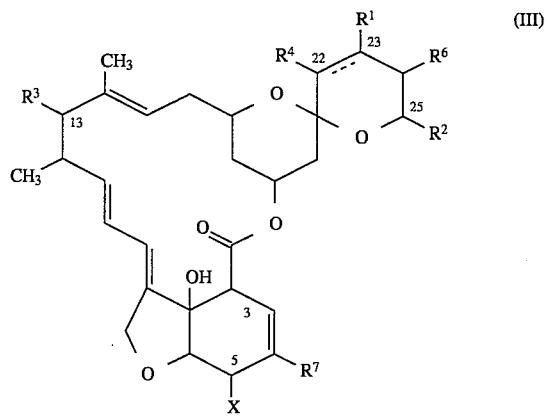

where $R^1$, $R^2$, $R^3$, $R^4$, $R^6$ and $R^7$ are as defined above and X is a leaving group such as fluoro, chloro, bromo, iodo, phenoxy optionally substituted with at least one electron-withdrawing group such as p-nitro, and sulphonic acid groups such as methanesulphonyloxy and p-toluenesulphonyloxy. Elimination of the leaving group at the 5-position results in formation of the compound of formula (II) and addition of cyanide thereto gives a compound of formula (I), the cyano group being attached to the nucleus of the molecule at the 3-position. It has been found that isolation of the intermediate compound of formula (II) is not generally necessary. Thus, treatment of the compound (III) with an ionic cyanide such as lithium cyanide in a non-aqueous solvent such as dimethylformamide results in elimination of the leaving group and formation of compound (I) in a single reaction step. The reaction may generally be conducted at room temperature. The compound of formula (I) may be isolated from the reaction mixture and purified by conventional methods, for example by solvent extraction followed by chromatography.

Compound (III) in which X is a leaving group may be prepared from the corresponding compounds in which X is OH by conventional methods, for example by treating the 5-OH compound with e.g. 2-nitrobenzenesulphonyl chloride in a basic solvent such as pyridine to form the 5-Cl compound. The product of formula (III) may be isolated from the reaction mixture by conventional methods.

It has been found that, when the leaving group is, for example, p-nitrophenoxy, the intermediate compound (III) need not be isolated and the compound of formula (I) may be prepared, from the compound in which X is OH, by a "one-pot" process in which the starting compound is converted to the p-nitrophenoxy derivative which is then treated with the cyanide while still in the original reaction solution.

The starting materials of formula (III) in which X is OH, comprising different combinations of substituents $R^1$–$R^7$, may generally be made by methods known in the art and discussed in the above-mentioned publications. It is believed that the above-described method of the invention is applicable to all compounds of formula (III) in which substituents $R^1$–$R^7$ are compatible with the reagents used. However in some instances it may be necessary or desirable to replace some of the $R^1$–$R^7$ substituents with other substituents after conversion of the formula (III) starting material to the 3-cyano compound. Such conversions may also be carried out by methods known in the art and as described in the published patent documents and other documents herein mentioned.

As previously mentioned the compounds of the invention are highly active antiparasitic agents. Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect animals and humans including gastro-intestinal parasites such as Ancylostoma, Necator, Ascaris, Strongyloides, Trichinella, Toxocara, Capillaria, Trichuris, Enterobius and parasites which are found in the blood or other tissues and organs such as filarial worms and the extra-intestinal stages of Strongyloides, Trichinella and Toxocara.

The compounds are also of value in treating ectoparasite infections including in particular arthropod ectoparasites of humans, animals and birds such as ticks, mites, lice, fleas, blowfly, biting insects and migrating dipterous larvae which can affect cattle and horses.

The compounds of formula (I) may be administered as a formulation appropriate to the specific use envisaged and to the particular species of host animal being treated and the parasite or insect involved. For use as an anthelmintic the compounds may be administered by injection, either subcutaneously or intramuscularly, alternatively they may be administered orally in the form of a capsule, bolus, tablet, chewable tablet or liquid drench, or they may be administered as a topical formulation or as an implant. For topical application dip, spray, powder, dust, pour-on, spot-on, jetting fluid, shampoos, collar, tag or harness may be used. Such formulations are prepared in a conventional manner in accordance with standard veterinary practice. Thus capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredient in an aqueous solution together with dispersing or wetting agents and injectable formulations may be prepared in the form of a sterile solution or emulsion. Pour-on or spot-on formulations may be prepared by dissolving the active ingredient in an acceptable liquid carrier vehicle, such as butyl digol, liquid paraffin or non-volatile ester with or without addition of a volatile component such as isopropanol. Alternatively, pour-on, spot-on or spray formulations can be prepared by encapsulation to leave a residue of active agent on the surface of the animal. These formulations will vary with regard to the weight of active compound depending on the species of host animal to be treated, the severity and type of infection and the body weight of the host. The compounds may be administered continuously, particularly for prophylaxis, by known methods. Generally for oral, parenteral and pour-on administration a dose of from about 0.001 to 10 mg per kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, pour-on formulations, emulsions and the like in accordance with standard agricultural practice.

For human use the compounds are administered as a pharmaceutically acceptable formulation in accordance with normal medical practice.

The compounds are also useful against insect pests of stored grains such as Tribolium sp., Tenebrio sp., and of agricultural plants such as spider mites, (Tetranychus sp.) aphids, (Acyrthiosiphon sp.), against migratory orthopterans such as locusts and immature stages of insects living on plant tissue. The compounds are useful as nematocides for the control of soil nematodes and plant parasites such as Meloidogyne sp. which may be of importance in agriculture. The compounds are active against other plant pests such as the southern army worm and Mexican bean beetle larvae.

For use as insecticides the compounds are applied as sprays, dusts, emulsions, pour-on formulation and the like in accordance with standard veterinary practice.

The invention is illustrated by the following Examples, in which "avermectin B2" refers to an avermectin having an OH substituent at the 23 position and a single bond at the 22–23 position, and "avermectin B1" refers to an avermectin having a double bond at the 22–23 position.

EXAMPLE 1

5-Chloro-5-deoxy-25-cyclohexlavermectin B2

To a solution of 25-cyclohexylavermectin B2 (20 g), obtained as described in EP-A-214731, in pyridine (100 ml) maintained at 0° C. was added, portionwise, over a period of 30 minutes, 2-nitrobenzenesulphonyl chloride (45 g). The reaction mixture was stirred for 1 hour during which time it was allowed to warm to room temperature. It was then poured into ethyl acetate (1000 ml) and aqueous hydrochloric acid (500 ml, 1N). The organic layer was separated, dried ($MgSO_4$) and evaporated to give an oil which was taken up in dichloromethane (100 ml) and applied to a column of silica gel (1 Kg). Elution with dichloromethane: methanol— 100:0 to 95:5—afforded, following combination and evaporation of suitable fractions, the title compound (12 g) which was characterised by mass and nmr spectroscopy.

EXAMPLE 2

3-Cyano-5-deoxy-25-cyclohexylavermectin B2

To a solution of 5-chloro-5-deoxy-25-cyclohexylavermectin B2 (20 g) from Example 1 in dimethylformamide (200 ml) was added a solution of lithium cyanide in dimethylformamide (200 ml, 0.5M). The mixture was stirred at room temperature for 24 hours. The reaction mixture was poured into water (750 ml) and ether (1500 ml). The organic layer was separated, washed with water (500 ml, ×2) and brine (500 ml), then dried ($MgSO_4$) and evaporated to yield an oil (25 g). The oil was taken up in ether (50 ml) and applied to a column of silica gel (1Kg). Elution with ether gave, after combination and evaporation of appropriate fractions, a white powder (5.1 g). This was further purified by reverse-phase high performance liquid chromatography on a Dynamax (trade mark) 2" diameter ODS C18 column eluting with methanol:water 80:20. Combination and evaporation of appropriate fractions gave a white, amorphous powder (2.38 g) which was further purified by reverse-phase high performance liquid chromatography on a Dynamax (trade mark) 2" diameter ODS Cl8 column eluting with acetonitrile:methanol:water 65:5:30. Combination and evaporation of appropriate fractions gave the title compound as a white, amorphous powder which was characterised by mass and nmr spectroscopy.

EXAMPLES 3 and 4

3-Cyano-5-deoxy-25-cyclohexylavermectin B2 monosaccharide and 3-cyano,5-deoxy-25-cyclohexylavermectin B2 aglycone 3-Cyano-5-deoxy-25-cyclohexylavermectin B2 (290 mg) from Example 2 was dissolved in isopropanol containing 1% of sulphuric acid (6 ml) and the solution left at room temperature for 24 hours. The reaction mixture was then poured onto ice (15 g) and water (15 ml) and extracted with dichloromethane (20 ml, ×2). The combined organic extracts were washed with aqueous potassium hydrogen carbonate solution, dried ($Na_2SO_4$) and evaporated to yield an off-white solid (280 mg). This was purified by reverse-phase high performance liquid chromatography on a Dynamax (trade mark) 2" diameter ODS C18 column eluting with acetonitrile:methanol:water (57:13:30). Combination and evaporation of appropriate fractions gave the title monosaccharide (105 mg) and aglycone (7 mg) as amorphous, white powders which were characterised by mass and nmr spectroscopy.

EXAMPLE 5

5-Chloro-5-deoxy-23-methoxy-25-cyclohexyl-22,23-dihydroavermectin B1

To a solution of 23-methoxy-25-cyclohexyl-22,23-dihydroavermectin B1 (50 g) as described in International Patent Application PCT/EP93/0036 in pyridine (250 ml) at 0° C. was added ortho-nitrobenzenesulphonyl chloride (25 g) and the mixture was stirred for 1 hour during which time it was allowed to warm to room temperature. The reaction mixture was partitioned between ethyl acetate (1000 ml) and aqueous hydrochloric acid (500ml, 1N). The organic phase was separated, washed with water (250 ml, ×2), dried ($MgSO_4$) and evaporated. The crude product was taken up in dichloromethane and applied to a column of silica gel (1Kg). Elution with dichloromethane:methanol—100:0 to 99:1—afforded, following combination and evaporation of suitable fractions, the title compound (55 g) which was characterised by mass and nmr spectroscopy.

EXAMPLE 6

3-Cyano-5-deoxy-23-methoxy-25-cyclohexyl-22,23-dihydroavermectin B1

To a solution of 5-chloro-5-deoxy-23-methoxy-25-cyclohexyl- 22,23-dihydroavermectin B1 (10.1 g) in dimethylformamide (55 ml) was added a solution of lithium cyanide in dimethylformamide (55 ml, 0.5M). The mixture was stirred at room temperature for 24 hours. The reaction mixture was then poured into ether (500 ml) and water (250 ml). The organic layer was separated. The aqueous layer was extracted with ether (250 ml, ×2).

The combined organic layers were then washed with water (250 ml), then saturated aqueous sodium chloride solution (250 ml), dried ($MgSO_4$) and evaporated to give a yellow foam (8.4 g). This was taken up in the minimum volume of ether and applied to a column of silica gel (1 Kg). Elution with ether:hexane—2:1 to 4:1—gave, after combination and evaporation of appropriate fractions, a white powder (2 g). This was further purified by reverse-phase high performance liquid chromatography on a Dynamax (trade mark) 2" diameter ODS C18 column eluding with water:methanol:acetonitrile—15:20:65. Combination and evaporation of appropriate fractions gave the title compound as a white, amorphous powder which was characterised by mass and nmr spectroscopy.

EXAMPLES 7 and 8

3-Cyano-5-deoxy-23-methoxy-25-cyclohexyl-22,23-dihydroavermectin B1 monosaccharide and 3-cyano-5-deoxy-23-methoxy-25-cyclohexyl-22,23-dihydroavermectin B1 aglycone 3-Cyano-5-deoxy-23-methoxy-25-cyclohexyl-22,23-dihydroavermectin B1 (285 mg) was dissolved in isopropanol containing 1% of sulphuric acid (6 ml) and the solution was left at room temperature for 24 hours. The reaction mixture was then poured onto ice (15 g) and water (15 ml) and extracted with dichloromethane (20 ml, ×2). The combined organic extracts were washed with aqueous potassium hydrogen carbonate solution, dried ($MgSO_4$) and evaporated to yield a white solid (280 mg). This was purified by reverse-phase high performance liquid chromatography on a Dynamax (trade mark) 2" diameter ODS C18 column eluted at 45 ml/min with water:methanol: acetonitrile—20:15:65 for 36 mins, then 18:17:65. Fractions were collected between 26 and 30 minutes and between 42 and 54 minutes. Combination and evaporation of appropriate fractions gave the title monosaccharide (65 mg) and aglycone (3 mg) as amorphous, white powders which were characterised by mass and nmr spectroscopy.

EXAMPLE 9

4"-oxo-3-cyano-5-deoxy-23-methoxy-25-cyclohexyl 22,23-dihydroavermectin B1

A mixture of 3-cyano-5-deoxy-23-methoxy-25-cyclohexyl- 22,23-dihydro-avermectin B1 (560 mg), tetra-npropylammonium perruthenate (56 mg), N-methylmorpholine oxide (560 mgs) and dichloromethane (15 ml) was stirred overnight. Further N-methylmorpholine-N-oxide (100 mg) and tetra-n-propylammonium perruthenate (10 mg) were added and stirring continued overnight. The mixture was added to a silica column (50 g). The column was eluted with dichloromethane:ethyl acetate—100:0 to 80:20. Combination and evaporation of appropriate fractions gave the title compound (410 mg) which was characterised by mass and nmr spectroscopy.

EXAMPLE 10

(E and Z]-4"-Oximino-3-cyano-5-deoxy-23-methoxy-25-cyclohexyl- 22,23-dihydroavermectin B1

A mixture of 4"-oxo-3-cyano-5-deoxy-23-methoxy-25-cyclohexyl- 22,23-dihydroavermectin B1 (510 mg), hydroxylamine hydrochloride (500 mg) and pyridine (10 ml) was stirred at room temperature overnight. The reaction mixture was poured into water (50 ml) and extracted with ether (50 ml, ×2). The combined organic layers were washed with aqueous citric acid (25 ml, 10%), water (25 ml), dried ($MgSO_4$) and evaporated to give the crude oximes (500 mg). The crude product was purified by reverse-phase high performance liquid chromatography on a Dynamax (trade mark) 2" diameter ODS C18 column eluted at 45 ml/min with water:methanol:acetonitrile 30:5:65 for 44 minutes, then 28:7:65 for 12 minutes, then 26:7:65 for 4 minutes, then 25:10:65 for 16 minutes, then 20:15:65 for 9 minutes, then 15:20:65 for 41 minutes. Fractions were collected between 92 and 116 minutes. Combination and evaporation of appropriate fractions gave a white powder (290 mg) which was further purified by reverse-phase high performance liquid chromatography on a Dynamax (trade mark) 2" diameter ODS C18 column eluted at 45 ml/min with water:methanol:acetonitrile— 25:10:65 for 72 minutes, then 15:20:65 for 28 minutes. Fractions were collected between 72 and 100 minutes. Combination and evaporation of appropriate fractions gave the title compounds as a white powder which were characterised by mass and nmr spectroscopy.

EXAMPLE 11

13-Chloro-13-deoxy-3-cyano-5-deoxy-23-methoxy-25-cyclohexy- 1-22,23-dihydroavermectin B1 aglycone To a stirred solution of 3-cyano-5-deoxy-23-methoxy-25-cyclohexyl-22,23-dihydroavermectin B1 aglycone (300 mg) in dichloromethane (10 ml) at 0° C containing 4-dimethylaminopyridine (230 mg) and di-isopropylethylamine (0.33 ml) was added a solution of 2-nitrobenzenesulphonyl-chloride (240 mg) in dichloromethane (3 ml). The reaction mixture was allowed to warm to room temperature and stirred overnight. The mixture was poured onto ice (15 g) and water (15 ml), acidified with aqueous citric acid (10%) and extracted with dichloromethane (20 ml, ×2). The combined organic layers were extracted with aqueous potassium hydrogen carbonate solution (20 ml), dried ($Na_2SO_4$) and evaporated to give an orange foam (360 mg). This was purified by column chromatography on silica gel (20 g) eluted with dichloromethane:ethyl acetate—100:0 to 95:5. Combination of appropriate fractions gave 80 mg of material which was further purified by reverse-phase high performance liquid chromatography on a Dynamax (trade mark) 1" column eluted with water:methanol—15:85. Combination of appropriate fractions gave 50 mg of compound which was further purified under the same conditions to 13 mg of material which was chromatographed on a silica gel (5 g) column eluted with dichloromethane: ethyl acetate 100:0 to 98:2. Combination of appropriate fractions gave the title compound (10 mg) as white powder which was characterised by mass and nmr spectroscopy.

EXAMPLE 12

3-Cyano-5,13-dideoxy-23-methoxy-25-cyclohexyl-22,23-dihydroavermectin B1 aglycone To a solution of 13-deoxy-23-methoxy-25-cyclohexyl-22,23-dihydroavermectin B1 aglycone (1.2 g) in dry pyridine (10 ml) was added 2-nitrobenzenesulphonyl chloride (1 g) and the mixture was maintained at room temperature for 1 hour. The solvent was then removed and the residue partitioned between ether (50 ml) and hydrochloric acid (50 ml, 5%). The organic layer was separated, washed with water, then brine, and then dried ($MgSO_4$) and evaporated to give 980 mg of a gum. This was taken up in dimethylformamide (8 ml) and a solution of lithium cyanide in dimethylformamide added (8 ml, 0.5M). The reaction mixture was allowed to stand for 24 hours then poured into ether (16 ml) and water (16 ml). The layers were separated. The aqueous layer was extracted with ether (16 ml, ×3). The combined organic layers were washed with brine (20 ml, saturated), dried ($MgSO_4$) and evaporated to give a dark oil (0.91 g).

The oil was taken up in ether and filtered through a plug of silica gel using further volumes of ether to elute the product. Evaporation gave a pale yellow foam (0.6 g). This was further purified by column chromatography on silica gel (100 g) eluted with hexane:ether —9:1 to 3:1. Combination and evaporation of appropriate fractions gave a white foam (110 mg). This was taken up in the minimum volume of methanol from which a white solid was deposited. This was filtered off and dried to yield the title compound (47 mg) which was characterised by mass and nmr spectroscopy.

EXAMPLE 13

3-Cyano-5-deoxy-23-ethoxy-5-cyclohexyl-22,23-hydroavermectin B1

A solution of 3-cyano-5-deoxy-25-cyclohexylavermectin B2 (350 mg) in ether (30 ml) containing ethyl iodide (1.75 ml) and a suspension of silver salicylate (1.4 g) was stirred at room temperature in the dark for 24 hours. The mixture was filtered and evaporated to give an oil (1.5 g) which was purified by reverse-phase high performance liquid chromatography on a Dynamax (trade mark) 2" diameter ODS C18 column eluted with a mixture of water:methanol—10:90. Combination and evaporation of appropriate fractions gave the title compound as a white solid (150 mg) which was characterised by mass and nmr spectroscopy.

EXAMPLE 14

3-Cyano-5-deoxy-23-ethoxy-25-cyclohexyl-22,23-dihydroavermectin B1 monosaccharide Method A A solution of 3-cyano-5-deoxy-23-ethoxy-25-cyclohexyl-22,23-dihydroavermectin B1 (45 mg) in isopropanol containing 1% of sulphuric acid (1 ml) was maintained at room temperature for 24 hours. The mixture was diluted with ether (20 ml), washed with saturated aqueous sodium hydrogen carbonate solution (20 ml), water (20 ml), dried ($MgSO_4$) and evaporated.

Method B

A solution of 3-cyano-5-deoxy-25-cyclohexyl-22,23-dihydro-avermectin B2 monosaccharide (120 mg) in ether (20 ml) containing ethyl iodide (0.5 ml) and a suspension of silver salicyclate (0.5 g) was stirred at room temperature in the dark for 24 hrs. A further 0.2 g of silver salicylate and 0.2 ml of ethyl iodide were then added and stirring continued for a further 72 hours. The mixture was filtered and evaporated.

The crude products from the above methods were combined and purified by reverse-phase high performance liquid chromatography on a Dynamax (trade mark) 2" diameter ODS C18 column eluted with water:methanol—15:85. Combination and evaporation of appropriate fractions gave the title compound as a white solid (120 mg) which was characterised by mass and nmr spectroscopy.

EXAMPLE 15

5-Chloro-5-deoxy-25-cyclohexyl-22,23-dihydroavermectin B1

To a solution of 25-cyclohexyl-22,23-dihydroavermectin B1 (8.1 g) as described in U.S. Pat. No. 5,089,480 in pyridine (40 ml) at 0° C. was added 2-nitrobenzenesulphonyl chloride (6 g). The mixture was stirred for 2 hours during which time it was allowed to warm to room temperature. The reaction mixture was poured into water (250 ml) and extracted with ethyl acetate (250 ml, ×2). The combined organic layers were washed with dilute aqueous hydrochloric acid, dilute aqueous sodium hydrogen carbonate solution and water. After drying (MgSO$_4$) evaporation of the solvents gave the title compound as a yellow foam (6.5 g) which was characterised by mass and nmr spectroscopy.

EXAMPLE 16

3-Cyano-5-deoxy-25-cyclohexyl-22,23-dihydroavermectin B1

To a solution of 5-chloro-5-deoxy-25-cyclohexyl- 22,23-dihydroavermectin B1 (8.2 g) in dimethylformamide (45 ml) was added a solution of lithium cyanide in dimethylformamide (45 ml, 0.5M). The mixture was stirred at room temperature for 24 hours. The work-up and open column chromatographic procedures described in Example 6 were employed to give a white powder (2 g). 500 mg of this material were further purified by reverse-phase high performance liquid chromatography on a Dynamax (trade mark) 2" diameter ODS C18 column eluted with a mixture of water:methanol:acetonitrile—5:30:65. Combination and evaporation of appropriate fractions gave the title compound as a white solid which was characterised by mass and nmr spectroscopy.

EXAMPLES 17 and 18

3-Cyano-5-deoxy-25-Cyclohexy1-22,23-dihydroavermectin B1 monosaccharide and 3-cyano-5-deoxy-25-cyclohexy1-22,23-dihydroavermectin B1 aglycone A solution of 3-cyano-5-deoxy-25-cyclohexyl-22,23-dihydroavermectin B1 (330 mg) in isopropanol containing 1% of sulphuric acid (7 ml) was maintained at room temperature for 24 hours. The mixture was poured onto ice (15 g) and water (15 ml) and extracted with dichloromethane (20 ml, ×2). The combined organic layers were washed with water (20 ml), dried (MgSO$_4$) and evaporated to give a gum (330 mg) which was purified by reverse phase high performance liquid chromatography on a Dynamax (trade mark) 2" diameter ODS C18 column eluted at 45 ml/min with water:methanol:acetonitrile —20:15:65 for 30 minutes, then 18:17:65 for 24 minutes, then 16:19:65 for 10 minutes, then 15:20:65 for 22 minutes. Fractions were collected between 44 and 48 minutes and 72 and 86 minutes. Combination and evaporation of appropriate fractions gave the title monosaccharide (120 mg) and aglycone (5 mg) as white solids which were characterised by mass and nmr spectroscopy.

EXAMPLE 19

3-Cyano-5,13-dideoxy-25-cyclohexyl-22,23-dihydroavermectin B1 aglycone

To a solution of 13-deoxy-25-cyclohexyl-22,23-dihydroavermectin B1 aglycone (0.486 g), as described in EP-A-214731, in dry pyridine (4 ml) at 0° C. was added 2nitrobenzenesulphonylchloride (0.38 g) and mixture was stirred for 2 hours. The pyridine was then removed and the residue was partitioned between ether and dilute aqueous hydrochloric acid (2.5%). The organic layer was separated, washed with water, then brine, dried (MgSO$_4$) and evaporated to give a foam (0.43 g). The foam was dissolved in dimethylformamide (3.7 ml) and a solution of lithium cyanide in dimethylformamide (3.7 ml, 0.5M) added. The reaction mixture was allowed to stand for 24 hours and then partitioned between ether and water. The aqueous layer was separated and extracted with three portions of ether. The combined ether extracts were dried (MgSO$_4$) and evaporated to give a foam (0.3 g). The foam was taken up in ether (minimum volume) and applied to column of silica gel (60 g). After elution with ether:hexane— 1:2 to 1:1—combination and evaporation of appropriate fractions gave a foam (0.23 g) which was taken up in ether (minimum volume) and applied to a column of silica gel (40 g). After elution with hexane:ether—9:1 combination and evaporation of appropriate fractions gave a solid (65 mg) which was further purified by reverse-phase high performance liquid chromatography on a Zorbax (trade mark) 1" diameter ODS C18 column eluted with methanol:water—90:10. Combination and evaporation of appropriate fractions gave the title compound as a white solid which was characterised by mass and nmr spectroscopy.

EXAMPLE 20

4'-Oxo-3-cyano-5-deoxy-25-cyclohexyl,-22,23-dihydroavermectin B1 monosaccharide To a stirred solution of 3-cyano-5-deoxy-25-cyclohexyl-22,23-dihydroavermectin B1 monosaccharide (350 mg) in dichloromethane (10 ml) under an atmosphere of nitrogen at room temperature was added powdered 4Å molecular sieves (10 mg), N-methylmorpholine oxide (350 mg) and tetra-n-propylammonium perruthenate (35 mg). After 2 hours N-methylmorpholine oxide (175 mg), tetra-n-propylammonium perruthenate (17 mg) and powdered 4Å molecular sieves (10 mg) were added and the mixture was stirred overnight. N-methylmorpholine oxide (80 mg), tetra-n-propylammonium perruthenate (8 mg were added and stirring continued for 2 hours. N-methylmorpholine oxide (80 mg), tetra-n-propylammonium perruthenate (8 mg) and powdered 4Å molecular sieves (10 mg) were added and stirring continued for 2 hours. The reaction mixture was then poured onto a column of silica gel (10 g) and eluted with dichloromethane. Combination and evaporation of appropriate fractions gave the title compound (230 mg) as a colourless glass which was characterised by mass and nmr spectroscopy.

EXAMPLE 21

4'-epi-Hydroxy-3-cyano-5-deoxy-25-cyclohexyl-22,23-dihydroavermectin B1 monosaccharide To a stirred solution of 4'-oxo-3-cyano-5-deoxy-25-cyclonexyl- 22,23-dihydroavermectin B1 monosaccharide (110 mg) in methanol (2 ml) at room temperature was added sodium borohydride (2 mg). After 30 minutes the reaction mixture was partitioned between ether and water. The organic layer was separated, washed with water, dried (MgSO$_4$) and evaporated to a gum (96 mg). The product was purified by reverse-phase high performance liquid chromatography on a Dynamax (trade mark) 1" diameter ODS C18 column eluted at 20 ml/min water:methanol:acetonitrile—20:15:65. Combination and evaporation of appropriate fractions gave the title compound (50 mg) as a white solid which was characterised by mass and nmr spectroscopy.

EXAMPLE 22

4'-Oximino-3-cyano-5-deoxy-25-cyclohexyl-22,23-dihydroavermectin B1 monosaccharide To a stirred solution of 4'-oxo-3-cyano-5-deoxy-25-cyclohexyl- 22,23-dihydroavermectin B1 monosaccharide (100 mg) in pyridine (2 ml) was added hydroxylamine hydrochloride (100 mg) and the mixture maintained at room temperature for 4 hours and then 4° C. for 48 hours. The reaction mixture was then partitioned between ether and water. The organic layer was separated and washed with saturated aqueous citric acid, saturated aqueous sodium hydrogen carbonate, water, then dried ($MgSO_4$) and evaporated. The crude product so obtained (100 mg) was purified by reverse-phase high performance liquid chromatography on a Dynamax (trade mark) 1" diameter ODS C18 column eluted at 20 ml/min with water:methanol: acetonitrile—20:15:65. Combination and evaporation of appropriate fractions gave the title compound (13 mg) as a white solid which was characterised by mass and nmr spectroscopy.

EXAMPLE 23

4'-epi-Methylamino-4',5-dideoxy,3-cyano-25-cyclohexyl- 22,23-dihydroavermectin B1 monosaccharide To a stirred solution at room temperature of 4'-oxo-3-cyano-5-deoxy-25-cyclohexyl-22,23-dihydroavermectin B1 monosaccharide (0.2 g) in methanol (1 ml) containing 0.85 ml of a solution prepared by mixing methanol (10 ml), glacial acetic acid (0.7 ml) and methylamine in industrial methylated spirits (1.33 ml of 33%) was added sodium cyanoborohydride (12 mg) in six equal portions over a period of 2 hours. A further 5 mg of sodium cyanoborohydride was added in 3 portions during the next hour and then a further 8 mgs in one portion. Stirring was continued for 30 minutes then the reaction mixture was partitioned between ethyl acetate and water. The organic layer was washed with brine. The aqueous layer was extracted with ethyl acetate. The combined organic layers were dried ($MgSO_4$) and evaporated to a gum (170 mg). The gum was taken up in the minimum volume of dichloromethane and applied to a column of silica gel (40 g). Combination and evaporation of appropriate fractions obtained after elution with dichloromethane: ethyl acetate —100:0 to 0:100 gave the title compound as a gum. The gum was dissolved in methanol (1 ml) and water (0.1 ml) added. Evaporation gave the title compound (30 mg) as a white solid.

EXAMPLE 24

23-Methylamino-3-cyano-5-deoxy-25-cyclohexyl-22,23-dihydroavermectin B1

To a stirred solution of 3-cyano-5-deoxy-25-cyclohexylavermectin B2 (230 mg) in dichloromethane (10 ml) was added pyridinium dichromate (230 mg). After 24 hours pyridinium dichromate (230 mg) was added. After a further 4 hours pyridinium dichromate (460 mg) was added and stirring continued for a further 24 hours. The reaction mixture was filtered and evaporated. The residue (210 mgs) was dissolved in dioxan (12 ml) and acetic acid (3.2 ml) and methoxylamine hydrochloride (70 mg) added. After 48 hours the mixture was poured into ethyl acetate (50 ml) and extracted with saturated aqueous sodium hydrogen carbonate solution, water, then dried ($MgSO_4$) and evaporated. The residue (120 mg) was purified by reverse-phase high performance liquid chromatography on a Dynamax (trade mark) 2" diameter ODS C18 column eluted with water:methanol—15:85. Combination and evaporation of appropriate fractions gave the title compound (37 mg) as a white solid which was characterised by mass and nmr spectroscopy.

EXAMPLE 25

23-Methoximino-3-cyano-5-deoxy-25-cyclohexyl-22,23-dihydroavermectin B1 monosaccharide A solution of 23-methoximino-3-cyano-5-deoxy-25-cyclohexyl- 22,23-dihydroavermectin B1 (13 mg) in isopropanol containing 1% of sulphuric acid (0.32 ml) was left to stand for 24 hours. The mixture was then diluted with ether (10 ml) and washed with saturated aqueous sodium hydrogen carbonate solution, water, then dried ($MgSO_4$) and evaporated. The product was purified by reverse-phase high performance liquid chromatography on a Beckmann (trade mark) ½ diameter ODS C18 column eluted with water:methanol—15:85. Combination and evaporation of appropriate fractions gave the title compound (4.8 mg) as a white solid which was characterised by mass and nmr spectroscopy.

EXAMPLE 26

13-oxo-3-cyano-5-deoxy-25-cyclohexyl-22,23-dihydroavermectin aglycone

To a stirred solution of 3-cyano-5-deoxy-25-cyclohexyl-22,23-dihydroavermectin B1 aglycone (0.8 g) in dimethylformamide (30 ml) at room temperature was added pyridinium dichromate (5 g). After 3 hours the reaction mixture was poured into water and extracted three times with ether. The combined ether extracts were washed with water then brine. After drying over $MgSO_4$ and evaporating the product was purified by silica gel column chromatography using ether:petrol ether —1:1 as eluent. Combination and evaporation of appropriate fractions gave the title compound (0.62 g) as a pale yellow foam which was characterised by mass and nmr spectroscopy.

EXAMPLE 27

13-Methoximino-3-cyano-5,13-dideoxy-25-cyclohexyl-22,23-dihydroavermectin B1 aglycone A solution of methoxylamine hydrochloride (1.5 g) in water (10 ml) was added over 5 minutes to a stirred solution of 13-oxo-3-cyano-5-deoxy-25-cyclohexyl-22,23-dihydroavermectin B1 aglycone (300 mg) in methanol (10 ml) and dioxan (20 ml). After 7 days at room temperature the mixture was diluted with water and extracted three times with ether. The combined organic layers were washed with brine, dried ($MgSO_4$) and evaporated. The oily residue (400 mg) was purified by chromatography on silica gel (40 g) eluted with ether:hexane—1:1 to 4:1, then ether. Combination and evaporation of appropriate fractions gave a foam (167 mg) which was further purified by reverse-phase high performance chromatography on a Dynamax (trade mark) 1" diameter ODS C18 column eluted with water: methanol—15:85. Combination and evaporation of appropriate fractions gave the title compound (90 mgs) as a white solid which was characterised by mass and nmr spectroscopy.

EXAMPLES 28 and 29

(E and Z)-13-Oximino-3-cyano-5,13-dideoxy-25-cyclohexyl-22,23-dihydroavermectin B1 aglycone A solution of hydroxylamine hydrochloride (1.5 g) in water (10 ml) was added over 5 minutes to a stirred solution of 13-oxo-3-cyano-5-deoxy-25-cyclohexyl-22,23-dihydroavermectin B1 aglycone (300 mg) in methanol (10 ml) and dioxan (20 ml). After 7 days at room temperature the mixture was diluted with water and extracted three times with ether. The combined organic layers were washed with brine, dried ($MgSO_4$) and evaporated. The oily residue (350 mg) was purified by chromatography on silica (40 g) eluting with ether:hexane—3:2. Combination and evaporation of suitable fractions gave a foam which was further purified by reverse-phase high performance liquid chromatography on a Dynamax (trade mark) 1" diameter ODS c18 column eluted with methanol:water—79:21. Combination and evaporation of appropriate fractions gave the first eluted isomer of the title compound (13 mg) and second eluted isomer of the title compound (23 mg). Both isomers were characterised by their mass and nmr spectroscopy.

EXAMPLE 30

23-epi-Hydroxy-3-cyano-5-deoxy-25-cyclohexylavermectin B2

To a stirred solution of 3-cyano-5-deoxy-25-cyclohexylavermectin B2 (1 g), phenoxyacetic acid (1.64 g) and triphenylphosphine (2.83 g) in tetrahydrofuran (10 ml) at 0° C. was added diethylazodicarboxylate (1.8 ml) dropwise over 5 minutes. The reaction mixture was allowed to warm to room temperature. After 4 hours a saturated solution of ammonia in methanol (6 ml) was added. The precipitate was filtered off, the filtrate left overnight at room temperature and then evaporated. The residue was purified by column chromatography on silica gel (50 g) eluted with ether:hexane—50:50. Combination and evaporation of appropriate fractions gave a foam which was further purified by reverse-phase high performance liquid chromatography on a Dynamax (trade mark) 1" diameter ODS C18 column eluted with methanol:water—85:15. Combination and evaporation of appropriate fractions gave the title compound (38 mg) as a white solid which was characterised by mass and nmr spectroscopy.

EXAMPLE 31

5-Chloro-5-deoxy-25-cyclohexylavermectin B1

To a stirred solution of 25-cyclohexylavermectin B1 (5.7 g), as described in EP-A-214731, in pyridine (30 ml) at 0° C. was added 2-nitrobenzenesulphonyl chloride (2.85 g). After 2 hours 2-nitrobenzenesulphonyl chloride (2.85 g) was added and stirring continued at 0° C. for 1 hour. The reaction mixture was poured into water (250 ml) and extracted with ethyl acetate (250 ml, ×2). The combined organic layers were washed with dilute hydrochloric acid, saturated aqueous sodium hydrogen carbonate solution, then dried ($MgSO_4$) and evaporated to give the title compound as a yellow foam (6.5 g).

EXAMPLE 32

3-Cyano-5-deoxy-25-cyclohexylavermectin B1

To a stirred solution of 5-chloro-5-deoxy-25-cyclohexylavermectin B1 (5.8 g) in dimethylformamide (30 ml) was added a solution of lithium cyanide in dimethylformamide (30 ml, 0.5M). After 24 hours the reaction mixture was partitioned between ether and water. The aqueous layer was separated and extracted twice with ether. The combined organic layers were washed twice with water, then brine, then dried ($MgSO_4$) and evaporated to give a yellow solid (5.7 g). This was purified by column chromatography on silica gel (1Kg) eluted with hexane:ether—1:2 to 1:4. Combination and evaporation of appropriate fractions gave a foam (0.732 g) which was further purified by reverse-phase high performance liquid chromatography on a Dynamax (trade mark) 2" diameter ODS C18 column eluted with water:methanol:acetonitrile—15:20:65. Combination and evaporation of appropriate fractions gave the title compound (400 mg) as a white solid which was characterised by mass and nmr spectroscopy.

EXAMPLE 33

3-Cyano-5-deoxy-25-cyclohexylavermectin B1 monosaccharide

A solution of 3-cyano-5-deoxy-25-cyclohexylavermectin B1 (70 mg) in isopropanol containing sulphuric acid (1%) (2 ml) was maintained at room temperature for 16 hours. The reaction mixture was diluted with ether and extracted with dilute sodium hydrogen carbonate solution. The organic layer was dried ($Na_2SO_4$) and evaporated. The crude product (70 mg) was purified by reverse-phase high performance liquid chromatography on a Dynamax (trade mark) 1" diameter ODS C18 column eluted with methanol:water 85:15. Combination and evaporation of appropriate fractions gave the title compound as a white solid which was characterised by mass and nmr spectroscopy.

EXAMPLE 34

3-Cyano-4",23-Diacetyl-4",5-dideoxy-22,23-dihydro-25-cyclohexylavermectin B1

To a stirred solution of 3-cyano-5-deoxy-25-cyclohexylavermectin B2 (113 mg) in dichloromethane (5 ml) containing triethylamine (244 µl) at room temperature was added acetic anhydride (162 µl). After 1.5 hours triethylamine (244 µl), acetic anhydride (400 µl) and 4-dimethylaminopyridine (10 mgs) were added and stirring continued for a further 22 hours. The reaction mixture was diluted with dichloromethane (100 ml) and extracted with dilute aqueous citric acid solution. The organic layer was separated, dried ($Na_2SO_4$) and evaporated to yield a gum (230 mg) which was purified by reverse phase high performance chromatography on a Dynamax (trade mark) 2" diameter ODS C18 column eluted with water and methanol (9:91). Combination and evaporation of appropriate fraction gave the title compound as an amorphous white powder which was characterised by mass and nmr spectroscopy.

EXAMPLE 35

4'-O-Acetyl-3-cyano-5-deoxy-22,23-dihydro-25-cyclohexyl-avermectin B1 monosaccharide To a solution of 3-cyano-5-deoxy-22,23-dihydro-25-cycloavermectin B1 monosaccharide (35 mg) in dichloromethane (2 ml) was added acetic anhydride (0.1 ml) and triethylamine (0.1 ml) and the mixture was stirred at room temperature for 48 hours. The reaction mixture was then diluted with dichloromethane (20 ml) and extracted with dilute aqueous citric acid solution. The organic layer was separated, dried ($Na_2SO_4$) and evaporated. The resultant gum was taken up in ether (2 ml) and passed through a silica Sep-pak (trade mark). The eluate was evaporated and the crude product was further purified by reverse-phase high performance liquid chromatography on a Dynamax (trade mark) 1" diameter ODS C18 column eluted with methanol:water 91:9. Combination and evaporation of appropriate fractions gave the title compound (11 mg) as an amorphous white powder which was characterised by mass and nmr spectroscopy.

EXAMPLE 36

3-Cyano-5-deoxy-milbemycin D

To a stirred solution of milbemycin D (2 g), as described in U.S. Pat. No. 4,346,171, in pyridine (15 ml) at 0° C. was added, in seven equal portions of 30 minutes, 2-nitrobenzenesulphonyl chloride (1.5 g). After 2 hours the pyridine was evaporated and the residue partitioned between ether and dilute hydrochloric acid. The organic layer was washed with water, then brine, then dried ($MgSO_4$) and evaporated to a yellow foam (2.25 g). This was dissolved in dimethylformamide (18.5 ml) and a solution of lithium cyanide in dimethylformamide (18.5 ml, 0.5M) added. After stirring at room temperature for 24 hours the mixture was partitioned between ether and water. The aqueous layer was separated and extracted three times with ether. The combined ether extracts were dried ($MgSO_4$) and evaporated to an oil (1.8 g). This was purified by column chromatography on silica gel (400 g) eluted with ether:hexane—1:2 to 2:1. Combination and evaporation of appropriate fractions gave a foam which was further purified by column chromatography on silica gel (50 g) eluted with ether:hexane—1:9 to 1:3. Combination and evaporation of appropriate fractions gave upon trituration with hexane the title compound as a white solid which was characterised by mass and nmr spectroscopy.

EXAMPLE 37

5-Deoxy-3,4,22,23-tetrahydro-$\Delta^{2,3,4,5}$-25-cyclohexylavermectin B1 monosaccharide To a stirred solution of 22,23-dihydro-25-cyclohexylavermectin B1 monosaccharide (5.00 g), triphenylphosphine (3.46 g) and 4-nitrophenol (0.92 g) in anhydrous tetrahydrofuran (50 ml) at 0° C. was added diethylazodicarboxylate (2.3 ml). After 30 minutes triphenylphosphine (1.6 g) and diethylazodicarboxylate (2.0 ml) was added and stirring continued for a further 30 minutes during which time the reaction mixture was allowed to warm to room temperature. 1,8-Diazobicylo[5.4.0]undec-7-ene (8 ml) was added in four equal portions over 30 minutes and the mixture then diluted with ether (500 ml). The mixture was washed with aqueous citric acid (250 ml, x2), sodium hydroxide (250 ml, 2N, x2) and brine (250 ml, x2). Each aqueous layer was extracted with ether (200 ml). The combined organic layers were washed with brine (250 ml), dried ($Na_2SO_4$) and evaporated. The residue was purified by column chromatography on silica gel (100 g) eluted with hexane:ether—1:1 to 1:3. Combination and evaporation of appropriate fractions gave the title compound (1.78 g) as a pale yellow solid which was characterised by mass and nmr spectroscopy.

PREPARATION 1

13-Deoxy-25-cyclohexyl-22,23-dihydroavermectin B1 aglycone

The title compound was prepared from 25-cyclohexyl-22,23-dihydroavermectin B1, described in U.S. Pat. No. 5,089,480, by application of the procedures described in EP-A-002615 for the analogous defunctionalisation at position 13 of 22,23-dihydroavermectin B1a.

PREPARATION 2

13-Deoxy-23-methoxy-25-cyclohexyl-22,23-dihydroavermectin B1 glycone

The title compound was prepared from 23-methoxy-25-cyclohexyl- 22,23-dihydroavermectin B1, described in International Patent Application PCT/EP93/0036 by application of the procedures described in EP-A-0002615 for the analogous defunctionalisation at position 13 of 22,23-dihydroavermectin B1a.

I claim:

1. An avermectin or milbemycin derivative, having a cyano substituent at the 3-position, a double bond at the 3-4 position and no substituent at the 5-position of the molecule.

2. A formulation for treatment or prophylaxis of parasitic infections which comprises a compound according to claim 1.

3. A formulation for use as an insecticide or for treating agricultural pests which comprises a compound according to claim 1.

4. A method of treating agricultural pests which comprises applying an agricultural pest treating effective amount of a compound according to claim 1 to such pest.

5. A compound of the formula (I):

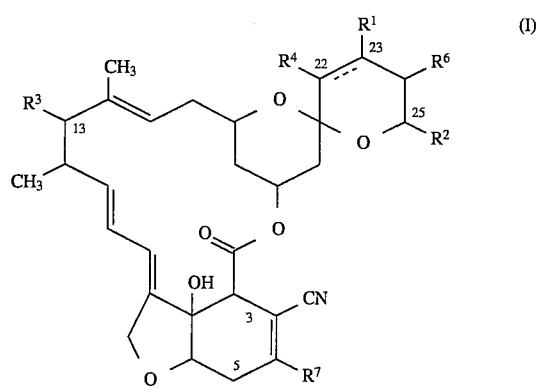

wherein the broken line represents an optional bond, $R^1$ and $R^4$ being absent when this bond is present, $R^1$ is H, OH, $C_1$–$C_8$ alkoxy optionally substituted by halo or by $C_1$–$C_4$ alkoxy, $C_2$–$C_5$ alkanoyl, $C_2$–$C_5$ alkoxy carbonyl, carboxy, mercapto or by aryl, or $R^1$ is $C_3$–$C_8$ alkenyloxy, $C_2$–$C_9$ alkylcarbonyloxy or $C_3$–$C_9$ alkenylcarbonyloxy, arylcarbonyl or arylcarbamoyl, said aryl optionally substituted by a $C_1$–$C_9$ alkyl group, or $R^1$ is attached to the remainder of the molecule by a double bond and is oxo or oximino optionally O-substituted by a $C_1$-$C_8$ alkyl, $C_2$-$C_8$ alkenyl or alkynyl, trialkylsilyl or aralkyl group, or is methylene optionally substituted by a cyano or $C_1$-$C_9$ alkyl group;

$R^4$ is H, OH or $C_1$-$C_8$ alkoxy, $C_1$-$C_9$ alkanoyloxy; =$CH_2$; oxo or optionally substituted oximino;

$R^2$ is (a) an alpha-branched $C_3$-$C_8$ alkyl, alkenyl, alkoxy-alkyl, or alkylthioalkyl group; an alpha-branched $C_4$-$C_8$ alkynyl group; a ($C_4$-$C_8$)cycloalkyl-alkyl group wherein the alkyl group is an alpha-branched $C_2$-$C_5$ alkyl group; a $C_3$-$C_8$ cycloalkyl or $C_5$-$C_8$ cycloalkenyl group, either of which may optionally by substituted by methylene or one or more $C_1$-$C_4$ alkyl groups or halo atoms; or a 3 to 6 membered oxygen or sulphur containing heterocyclic ring which may be saturated, or fully or partially unsaturated and which may optionally be substituted by one or more $C_1$-$C_4$ alkyl groups or halo atoms; or (b) a group of the formula —$CH_2R^8$ wherein $R^8$ is H, $C_1$-$C_8$ alkyl, $C_2$-$C_8$ alkenyl, $C_2$-$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_3$-$C_8$ cycloalkyl or $C_5$-$C_8$ cycloalkenyl group, either of which may optionally be substituted by methylene or one or more $C_1$-$C_4$ alkyl groups or halo atoms; or a 3 to 6 membered oxygen or sulphur containing heterocyclic ring which may be saturated, or fully unsaturated, or partially unsaturated and which may optionally be substituted by one or more $C_1$-$C_4$ alkyl groups or halo atoms; or a group of the formula $SR^9$ wherein $R^9$ is $C_1$-$C_8$ alkyl, $C_2$-$C_8$ alkenyl, $C_3$-$C_8$ alkynyl, $C_3$-$C_8$ cycloalkyl, $C_5$-$C_8$ cycloalkenyl, phenyl or substituted phenyl wherein the substituent is $C_1$-$C_4$ alkyl, $C_1$-$C_4$ alkoxy or halo; or (c) a $C_1$-$C_6$ alkyl group substituted by one oxo or one or more hydroxy groups or by a single oxygen atom on two adjacent carbon atoms forming an oxirane ring, or $R^2$ is a $C_1$-$C_5$ alkyl group substituted by a ($C_1$-$C_6$)alkoxy-carbonyl group, said substituents on $R_2$ being attached to either or both of a terminal carbon atom and a carbon atom adjacent a terminal carbon atom of $R^2$; or (d) =$CH_2$ or a group of the formula:

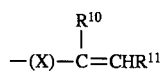

wherein $R^{10}$ and $R^{11}$ are both H; $R^{10}$ is H and $R^{11}$ is $C_1$-$C_3$ alkyl, or one of $R^{10}$ and $R^{11}$ is H and the other is phenyl, heteroaryl, $C_2$-$C_6$ alkoxycarbonyl or substituted phenyl or heteroaryl wherein said substituent is fluorine, chlorine, $C_1$-$C_4$ alkyl, $C_1$-$C_4$ alkoxy, $C_1$-$C_4$ alkylthio, hydroxy($C_1$-$C_4$)alkyl, cyano, aminosulphonyl, $C_2$-$C_6$ alkanoyl, $C_2$-$C_6$ alkoxycarbonyl, nitro, trifluoromethyl, trifluoromethoxy, amino or mono or di($C_1$-$C_4$)-alkylamino; and X is a direct bond or is an alkylene group having from 2 to 6 carbon atoms which may be straight or branched-chain; or (e) phenyl which may optionally be substituted with at least one substituent selected from $C_1$-$C_4$ alkyl, $C_1$-$C_4$ alkylthio groups, halo atoms, trifluoromethyl, and cyano;

or $R^2$ may be a group of formula (II):

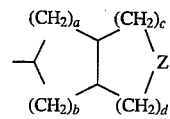

wherein Z is O, S or —$CH_2$— and a, b, c and d may each independently be 0, 1 or 2; the sum of a, b, c and d not exceeding 5;

$R^3$ is hydrogen, hydroxy, $C_1$-$C_8$ alkoxy or $C_2$-$C_8$ alkenoxy, $C_1$-$C_9$ alkanoyloxy or $C_2$-$C_9$ alkenoyloxy, aroyloxy, ($C_1$-$C_5$)alkyloxy-($C_1$-$C_5$)alkoxymethoxy, halogen, oxo, or optionally substituted oximino, hydrazono, carbazido or semicarbazido, N-($C_1$-$C_4$)alkyl semicarbazido, N,N-di($C_1$-$C_4$)alkylsemicarbazido, $C_1$-$C_5$ alkanoylhydrazido, benzoylhydrazido or ($C_1$-$C_4$)alkyl benzoylhydrazido; or $R_3$ is

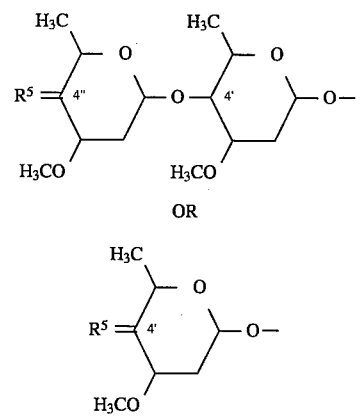

wherein $R^5$ is attached to C-4" or C-4' by a single bond and is hydrogen, halo, hydroxy, $C_1$-$C_9$ alkanoyloxy or $C_2$-$C_9$ alkenoyloxy, aroyloxy, $C_1$-$C_8$ alkoxy, amino, N-($C_1$-$C_8$) alkylamino, N,N-di($C_1$-$C_9$)alkylamino; N-($C_1$-$C_5$)alkanoylamino, or N,N-di($C_1$-$C_9$)alkanoylamino;

or $R^5$ is attached to C-4" or C-4' by a double bond and is oxo, oximino optionally substituted by a $C_1$-$C_8$ alkyl, $C_2$-$C_8$ alkenyl or alkynyl, trialkylsilyl or aralkyl group; semicarbazido, N-$C_1$-$C_4$ alkylsemicarbazido, N,N-di ($C_1$-$C_4$)alkyl-semicarbazido, $C_1$-$C_5$ alkanoylhydrazido, benzoylhydrazido, or ($C_1$-$C_4$) alkylbenzoylhydrazido;

$R^6$ is H or $C_1$-$C_6$ alkyl; and $R^7$ is methyl, hydroxymethyl, ($C_1$-$C_4$ alkoxy) -methyl, ($C_2$-$C_5$ alkanoyl)oxymethyl, ($C_2$-$C_5$ alkenoyl) oxymethyl, aryloxymethyl, aralkanoyloxymethyl, oxo, oximino optionally substituted by a $C_1$-$C_8$ alkyl, alkenyl, alkynyl, trialkylsilyl or aralkyl group, halomethyl, azidomethyl or cyanomethyl.

6. A compound according to claim 5, in which $R^1$ is H, OH, O-($C_1$-$C_4$)alkyl, O-($C_1$-$C_5$)alkanoyl, oxo, or oximino optionally substituted by $C_1$-$C_4$ alkyl or aryl($C_1$-$C_4$)alkyl.

7. A compound according to claim 6 in which $R^1$ is H, OH, $OCH_3$, $OC_2H_5$, $OCOCH_3$, oxo, oximino or methoximino.

8. A compound according to claim 5, in which $R^1$ and $R^4$ are both H.

9. A compound according to claim 5, in which $R^1$ and $R^4$ are absent and the optional bond is present.

10. A compound according to claim 5, 6 or 7 in which $R^4$ is H, OH, oxo or oximino.

11. A compound according to claim 10 in which $R^2$ is straight or branched chain alkyl, alkenyl, cycloalkyl or cycloalkenyl.

12. A compound according to claim 11 in which $R^2$ is methyl, ethyl, 2-propyl, 2-butyl, 2-buten-2-yl, 2-pentenyl, 4-methyl-2-penten-2-yl, or cyclohexyl.

13. A compound according to claim 12, in which $R^6$ and $R^7$ are both methyl.

14. A compound according to any of claims 2 to 10 in which $R^3$ is H or of formula:

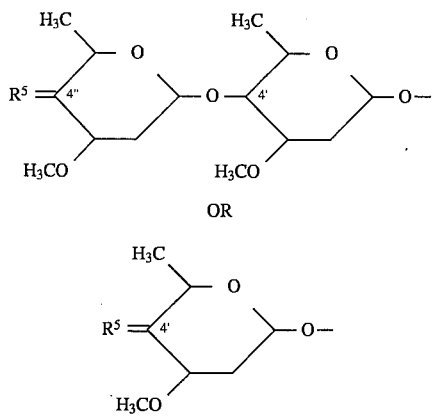

wherein $R^5$ is OH, $(C_1-C_4)$alkoxy, $(C_2-C_5)$alkanoyloxy, amino, N-$(C_1-C_4)$-alkylamino, N-$(C_1-C_5)$alkanoylamino, oxo or oximino optionally substituted by a $C_1-C_4$ alkyl group.

15. A compound according to claim 14 in which $R^3$ is H or of formula:

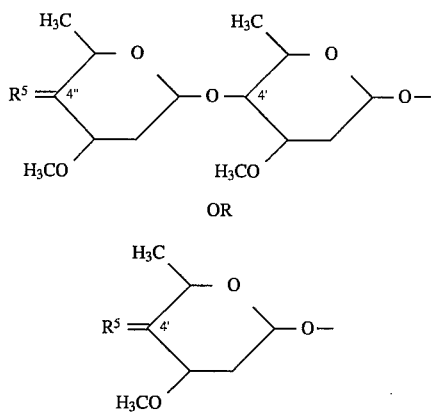

wherein $R^5$ is OH, $OCH_3$, $OC_2H_5$, $OCOCH_3$, methylamino, acetylamino, oxo, oximino or methoximino.

16. A compound according to claim 2, which is:
(i) 3-cyano-5-deoxy-25-cyclohexyl avermectin B2 or its monosaccharide, or
(ii) 3-cyano-5-deoxy-23-methoxy-25-cyclohexyl- 22,23-dihydroavermectin B1 or its monosaccharide, or
(iii) 4"-oximino-3-cyano-5-deoxy-23-methoxy-25-cyclohexyl- 22,23-dihydroavermectin B1; or
(iv) 3-cyano-5-deoxy-25-cyclohexyl-22,23-dihydroavermectin B1 or its monosaccharide, or
(v) 4'-epi-hydroxy-3-cyano-5-deoxy-25-cyclohexyl-22,23-dihydroavermectin B1 monosaccharide, or
(vi) 23-methoximino-3-cyano-5-deoxy-25-cyclohexyl-22,23-dihydroavermectin B1 or its monosaccharide; or
(vii) 3-cyano-5-deoxy-25-cyclohexylavermectin B1 or its monosaccharide; or
(viii) 3-cyano-5,13-dideoxy-23-methoxy-25-cyclohexyl-22,23-dihydroavermectin B1 aglycone; or
(ix) 3-cyano-5,13-dideoxy-25-cyclohexyl-22,23-dihydroavermectin B1 aglycone; or
(x) 3-cyano-5-deoxy-milbemycin D.

17. The compound according to claim 16 which is 3-cyano-5-deoxy-25-cyclohexyl avermectin B2.

18. The compound according to claim 16 which is 3-cyano-5-deoxy-25-cyclohexyl avermectin B2 monosaccharide.

19. A formulation for treatment or prophylaxis of parasitic infections which comprises a compound according to claim 5.

20. A formulation for use as an insecticide or for treating agricultural pests comprising a compound according to claim 5.

21. A method of treatment or prophylaxis of parasitic infections which comprises administering to a person or animal in need of such treatment an effective antiparasitic amount of a compound according to claim 5.

22. A method of treating agricultural pests which comprises applying an agricultural pest treating effective amount of a compound according to claim 5 to such pest.

23. A method of treatment or prophylaxis of parasitic infections which comprises administering to a person or animal in need of such treatment an effective antiparasitic amount of a compound according to claim 1.

24. A method of making a compound according to claim 1, which comprises allowing an avermectin or milbemycin derivative substituted at the 5-position with a leaving radical, or having no substituent at the 5-position and double bonds at the 2–3 and 4–5 positions, to react with an ionic cyanide.

25. A method according to claim 24, in which the leaving radical is fluoro, chloro, bromo, iodo or p-nitrophenoxy.

26. A method according to claim 24, in which an avermectin or milbemycin or derivative thereof having an —OH group at the 5-position of the molecule is converted to the corresponding derivative having a leaving radical at the 5-position and said corresponding derivative is allowed to react with an ionic cyanide without isolation of said corresponding derivative from the reaction medium.

27. A method of making a compound according to claim 5, which comprises allowing a compound of formula (II) or (III):

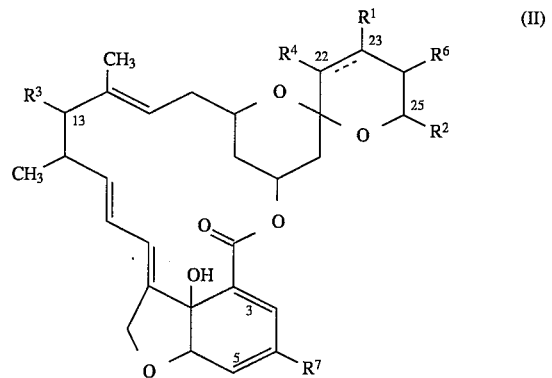

-continued

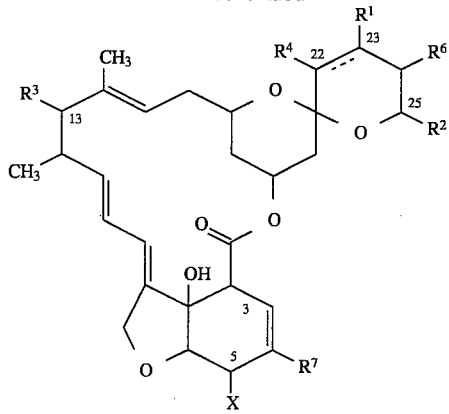
(III)

wherein $R^1$, $R^2$, $R^3$, $R^4$, $R^6$ and $R^7$ are as defined in claim 5 and X is a leaving radical to react with an ionic cyanide to make a compound of formula (I) and if necessary replacing or converting one or more of the $R^1$–$R^7$ substituents of the 3-cyano compound so made to produce a further compound of formula (I).

28. A method according to claim 27 in which the leaving radical is fluoro, chloro, bromo, iodo or p-nitrophenoxy.

29. A method according to claim 27 in which an avermectin or milbemycin or derivative thereof having an —OH group at the 5-position of the molecule is converted to the corresponding derivative having a leaving radical at the 5-position and said corresponding derivative is allowed to react with an ionic cyanide without isolation of said corresponding derivative from the reaction medium.

30. A compound of formula (II):

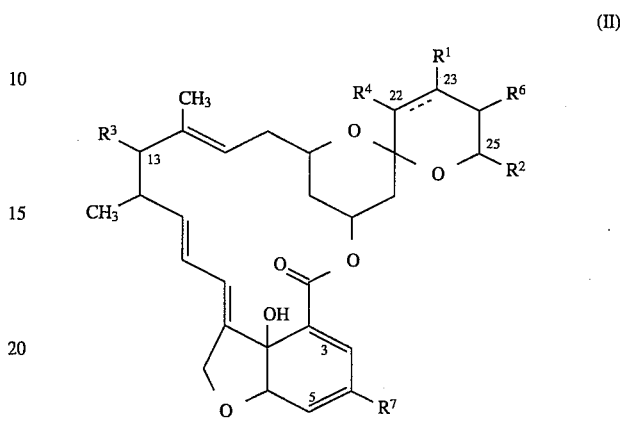
(II)

wherein $R^1$, $R^2$, $R^3$, $R^4$, $R^6$ and $R^7$ are as defined in claim 5.

* * * * *